US012778874B2

(12) United States Patent
Kohler Riedi et al.

(10) Patent No.: US 12,778,874 B2
(45) Date of Patent: Nov. 3, 2026

(54) CATALASE COMPOSITION WITH IMPROVED STABILITY AND METHODS

(71) Applicant: Solventum Intellectual Properties Company, Maplewood, MN (US)

(72) Inventors: Petra L. Kohler Riedi, Minneapolis, MN (US); Steven P. Swanson, Blaine, MN (US); Paul R. Klaiber, Mahtomedi, MN (US)

(73) Assignee: Solventum Intellectual Properties Company, Eagan, MN (US)

(*) Notice: Subject to any disclaimer, the term of this patent is extended or adjusted under 35 U.S.C. 154(b) by 982 days.

(21) Appl. No.: 17/948,642

(22) Filed: Sep. 20, 2022

(65) Prior Publication Data

US 2023/0110368 A1 Apr. 13, 2023

Related U.S. Application Data

(60) Provisional application No. 63/250,474, filed on Sep. 30, 2021.

(51) Int. Cl.

*A61K 8/66* (2006.01)
*A61K 8/22* (2006.01)
*A61Q 11/00* (2006.01)
*C12N 9/08* (2006.01)

(52) U.S. Cl.

CPC .................. *A61K 8/66* (2013.01); *A61K 8/22* (2013.01); *A61Q 11/00* (2013.01); *C12N 9/0065* (2013.01); *C12Y 111/01006* (2013.01)

(58) Field of Classification Search

CPC .................................... A61K 8/66; A61K 8/22
USPC ............................................ 424/49, 53, 401
See application file for complete search history.

(56) References Cited

U.S. PATENT DOCUMENTS

| | | | | |
|---|---|---|---|---|
| 3,535,421 | A | 10/1970 | Briner et al. | |
| 3,678,154 | A | 7/1972 | Widder et al. | |
| 4,720,352 | A * | 1/1988 | Petronella | C07C 51/412 554/71 |
| 5,356,800 | A | 10/1994 | Jaquess | |
| 6,685,921 | B2 | 2/2004 | Lawlor | |
| 6,958,080 | B2 | 10/2005 | Mitamura et al. | |
| 8,647,608 | B2 | 2/2014 | Yang et al. | |
| 10,653,594 | B2 | 5/2020 | Haeberlein et al. | |
| 2006/0051385 | A1 | 3/2006 | Scholz | |

FOREIGN PATENT DOCUMENTS

| | | | | |
|---|---|---|---|---|
| EP | 3214180 | A1 * | 9/2017 | C12Q 1/30 |
| GB | 1056192 | A | 1/1967 | |
| WO | 2012072777 | A1 | 6/2012 | |

OTHER PUBLICATIONS

Catalase 20,000, Powder catalase Enzyme, Nutraceutical Division, Specialty Enzymes & Biotechnologies, Jun. 2016, 1 page.
Costa, "Studies of Stabilization on native catalase using additives", Enzyme and Microbial Technology, 2002, vol. 30, pp. 387-391.
Galasso, "Browsing the oldest antioxidant enzyme: catalase and its multiple regulation in cancer", Free Radical Biology and Medicine, 2021, vol. 172, pp. 264-272.
Glorieux, "Catalase, a remarkable enzyme: targeting the oldest antioxidant enzyme to find a new cancer treatment approach", Biol. Chem. 2017, vol. 398, No. 10, pp. 1095-1108.
Kikuchi-Torii, Properties of Aspergillus niger Catalase, J. Biochem. 1982, vol. 92, No. 5, pp. 1449-1456.

* cited by examiner

*Primary Examiner* — Walter E Webb

(57) ABSTRACT

A method of removing calculus from a tooth is described comprising: applying aqueous compositions A and B to the tooth surface, wherein the composition A comprises hydrogen peroxide or a precursor thereto and composition B comprises catalase and a stabilizer comprising hydroxyl groups; and removing at least a part of the calculus from the tooth surface. Preferred stabilizers include dipropylene glycol and 1,3 propane diol. Also described are aqueous compositions and kits.

20 Claims, No Drawings

CATALASE COMPOSITION WITH IMPROVED STABILITY AND METHODS

BACKGROUND

Various catalase compositions and methods of use have been described. For example, U.S. Pat. No. 10,653,594 (Abstract) describes methods and kits for removing calculus from a tooth. The method includes applying a composition A comprising hydrogen peroxide or a precursor thereto to the tooth; applying a composition B comprising a catalase to the tooth, thereby generating oxygen; and removing at least a part of the calculus from the tooth; wherein the composition A is applied before or after the composition B is applied.

SUMMARY

Industry would find advantage is catalase compositions having improved stability.

In one embodiment, a method of removing calculus from a tooth is described comprising: applying aqueous compositions A and B to the tooth surface, wherein the composition A comprises hydrogen peroxide or a precursor thereto and composition B comprises catalase and a stabilizer comprising hydroxyl groups; and removing at least a part of the calculus from the tooth surface.

In another embodiment, aqueous compositions are described suitable for use for removing calculus from a tooth surface comprising catalase; and a stabilizer comprising hydroxyl groups.

In another embodiment, a kit is described comprising composition A comprises hydrogen peroxide or a precursor thereto; and composition B comprising an aqueous composition comprising catalase and a stabilizer comprising hydroxyl groups.

Preferred stabilizers include dipropylene glycol and 1,3 propane diol.

DETAILED DESCRIPTION

Dental calculus (also referred to as dental tartar) is defined as mineralized dental biofilm filled with crystals of various calcium phosphates or dental plaque that has partially or completely calcified. It may be caused by the continual accumulation of minerals from fluids in the oral environment on plaque on the teeth. Dental calculus is a common oral condition afflicting humans and a variety of animal species and the presence of dental calculus may lead to periodontal diseases. As described in U.S. Pat. No. 10,653,594; incorporated herein by reference, methods of removing dental calculus often rely predominantly upon mechanical means such as scaling, are time consuming and laborious for dental professionals, and can be a painful and unpleasant experience for patients.

In some embodiments, methods and kits for removing calculus from a tooth are described. Generally, the method comprises applying composition A, comprising a hydrogen peroxide or a hydrogen peroxide precursor, to the tooth; applying composition B, comprising catalase and a stabilizer comprising hydroxyl groups, to the tooth, thereby generating oxygen; and removing at least a part of the calculus from the tooth. The methods and kits can provide easier removal of dental calculus and/or reduce the time of calculus removal.

In some embodiments, composition A comprises hydrogen peroxide. The hydrogen peroxide can be generated by a peroxide generating enzyme in combination with the corresponding substrate, e.g., glucose oxidase and Superoxide Dismutase (SOD). For example, glucose oxidase can catalyze the oxidation of glucose to hydrogen peroxide. In some embodiments, the hydrogen peroxide may be in a form of a hydrogen peroxide adduct, such as carbamide peroxide, percarbonate salts or acids and polyvinylpyrrolidone (PVP) peroxide. Suitable percarbonate salts or acids can include, but are not limited to percarbonic acid, sodium percarbonate, potassium percarbonate, magnesium percarbonate, calcium percarbonate, zinc percarbonate.

In some embodiments, composition A comprises a hydrogen peroxide precursor, such as perborate salts or acids, metal peroxides, organic peroxide, inorganic peroxyacids or salts and combinations thereof. Suitable perborate salts or acids can include, but are not limited to perboric acid, sodium perborate, potassium perborate, magnesium perborate, calcium perborate, and zinc perborate. Suitable metal peroxides include, but are not limited to, calcium peroxide and magnesium peroxide. Suitable organic peroxides can include, but are not limited to peroxycarboxylic acids, such as peracetic acid or salts thereof, permalonic acid or salts thereof, pertartaric acid or salts thereof and percitric acid or salts thereof. In some embodiments, the organic peroxide can be a peracetate salt. Suitable inorganic peroxyacids or salts can include, but are not limited to peroxymonosulfuric acid, peroxyphosphoric acid and a potassium salt of a sulfuric peroxyacid.

In some embodiments, composition A comprises hydrogen peroxide having a concentration ranging from 0.003 M to 12 M. In typical embodiments, the hydrogen peroxide has a concentration no greater than 6, 5, 4, or 3M. In some embodiments, composition A comprises hydrogen peroxide in an amount of 0.01 wt. %, 0.1 wt. %, 1 wt. %, 5 wt. %, 10 wt. %, 30 wt. %, 35 wt. %, or any suitable range between and including any two of these values. In other embodiments, composition A comprises a hydrogen peroxide precursor or hydrogen peroxide adduct capable of producing the described concentration of hydrogen peroxide, for example, producing a concentration of at least 0.003 M hydrogen peroxide. In one illustrative example, a 15 wt. % carbamide peroxide solution can produce a solution comprising 5 wt. % hydrogen peroxide.

Catalases are classified into three types, based on their structure and function. Typical catalases and catalase-peroxidases contain heme prosthetic groups. The third type, manganese catalases, contain non-heme manganese groups. Catalase peroxidases constitute a protein family predominantly present among eubacteria and archaea, although two evolutionary branches are also found in the eukaryotic world. Typical catalases are commonly isolated from aerobic organisms, including animals, plants, fungi, and bacteria. Most typical catalases are composed of four subunits of equal size, with a molecular mass of 200-340 kDa, and contain four prosthetic groups. The human catalase is a typical catalase composed of small subunits (62 kDa) with a ferric protorphyrin.

Typical catalases include those produced by, but not limited to *Agrobacterium tumefaciens, Aliivibrio salmonicida, Anopheles gambiae, Aspergillus nidulans*, and *Aspergillus niger*. Suitable catalases that can be used in the present disclosure are well known in the art and can include those described in International Publication No. WO2012/072777. For example, suitable catalases can include catalase derived/isolated from bovine liver, *Aspergillus niger* and *Micrococcus* lysodeikticus. In some embodiments, catalase can be in an unisolated form, such as a part of or whole eukaryotic and prokaryotic organism. Catalases can catalyze the disproportionation of two molecules of hydrogen peroxide into two molecules water and one molecule oxygen.

In one embodiment, the catalase comprises *Aspergillus niger*. Catalase from *Aspergillus niger* can have a molecular weight of over 300 kDa. *Aspergillus niger* catalase is commercially available and is produced by fermentation of the fungus. In some embodiments, the catalase may be characterized as food grade and/or kosher and/or contain less than 20 ppm of heavy metals.

In some embodiments, the aqueous composition (e.g. composition B) can include greater than 3 units/mL of catalase. In some embodiments, the aqueous comprises greater than 15, 16, or 17 units/mL of catalase. One unit of catalase decomposes 1.0 μmole of hydrogen peroxide per minute at pH 7.0 at 25° C. While the catalase decomposes, the hydrogen peroxide concentration decreases from 10.3 to 9.2 mM, as measured by the rate of decrease of $A_{240}$. In some embodiments, the aqueous composition comprises catalase having an enzyme activity of at least of 100 units/mL, 300 units/mL, 500 units/mL, 750 units/mL, 1,000 units/mL, 2,000 units/mL 3,000 units/mL, 4,000 units/mL, 5,000 units/mL, 10,000 units/mL, 15,000 units/mL, 20,000 units/mL, 30,000 units/mL, 300,000 units/mL, or a range between and including any two of these values (e.g. 30 units/mL to 3,000 units/mL). A catalase having a higher enzyme activity can be diluted with water. For example, a catalase having an enzyme activity of 20,000 units/g can be diluted to an enzyme activity of 1,000 units/mL In some embodiments, after the aqueous composition (e.g. composition B) is applied to the tooth surface, the enzyme activity of catalase inside the oral cavity increases above the natural concentration/enzyme activity of catalase present inside the oral cavity prior to application of the aqueous composition (e.g. composition B). The increase can be at least 5 units/mL, 10 units/mL, 20 units/mL, 30 units/mL, or 50 units/mL as well as the previously described catalase concentrations or a range between and including any two of these values. It is appreciated that enzyme activity can vary within 15% of a specified value. Further the enzyme activity is typically about the same for temperatures ranging from room temperature (e.g. 25° C.) to body temperature (37° C.), as well as higher (e.g. storage) temperatures ranging up to 40, 45 or 50° C.

The aqueous composition of catalase (e.g. composition B) further comprises a stabilizer comprising hydroxyl groups. The stabilizer is typically present in an amount ranging from about 5 to about 15 wt. % of the total aqueous composition. The type and amount of (e.g. alcohol) stabilizer is preferably selected such that the aqueous composition comprising catalase (e.g. composition B) is sufficiently stable such that after storage for at least 75 days at 37° C., the composition (e.g. composition B) comprises less than 50 mg/L of hydrogen peroxide when reacted with a 3% hydrogen peroxide aqueous solution. In some embodiments, the aqueous composition comprising catalase (e.g. composition B) is sufficiently stable after storage for at least 90, 100, 120, 120, 130, 140 or 150 days at 37° C. or any suitable range between and including any two of these values.

The stabilizer may be characterized as an alcohol. The stabilizer typically comprises an alkylene or ether backbone and at least two hydroxyl groups.

Unlike, "fatty" alcohols, the alkylene or ether backbone is of a sufficiently small chain length such the stabilized is miscible with deionized water. For example, hexanol is poorly soluble in water. The alkylene or ether backbone typically has no greater than 3 or 4 carbon atoms. Although butanol has a water solubility of 12.5%, three carbon alcohols, such as dipropylene glycol have greater solubility with water. Dipropylene glycol is a mixture of three isomeric chemical compounds, 4-oxa-2,6-heptandiol, 2-(2-hydroxy-propoxy)-propan-1-ol, and 2-(2-hydroxy-1-methyl-ethoxy)-propan-1-ol. It is a colorless, nearly odorless liquid with a high boiling point (230.5° C.) and low toxicity. Propane diol is also miscible with water, having a boiling point ranging from 211 to 217° C. Thus, the boiling point of the stabilizer can be at least 175, 200, or 225° C., significantly greater than water and therefore does not volatilize during use.

Unlike glycerol, the stabilizer typically has a molecular weight per oxygen atom (e.g. of hydroxyl or ether group) of at least 32, 33, 34, 35, 36, 37, or 38 g/mole. The stabilizer typically has a molecular weight per oxygen atom (e.g. of hydroxyl or ether group) of no greater than 50, 49, 48, 47, 46, or 45 g/mole.

In some embodiments, propylene glycol was found to provide sufficient catalase stability at 32 days when present at a concentrations ranging from about 5 to 20 wt. % of the aqueous solution.

As described in the forthcoming examples, glycerol was not found to provide sufficient catalase stability as described above, when tested at 68 days. Since the storage stability of catalase and glycerol was not tested before the 68th day, glycerol may have failed prior to the 68th day.

In some embodiments, propylene glycol was found to provide sufficient stability at 32 days when present at a concentrations ranging from about 5 to 20 wt. % of the aqueous composition comprising catalase (e.g. composition B); yet insufficient stability at 66 days.

Preferred stabilizers include dipropylene glycol and 1,3 propane diol.

As demonstrated in the forthcoming examples, aqueous compositions of dipropylene glycol and catalase (e.g. composition B) were found to be sufficiently stable, as described above, for 42, 90, 97, 141, 146, and 222 days, or any suitable range between and including any two of these values. The concentration of dipropylene glycol is typically at least 5, 5.5, 6, 6.5, 7, 7.5, 8.5, 9, 9.5, or 10 wt. % of the aqueous solution. When the amount of dipropylene glycol exceeded 10 wt. %, the aqueous composition comprising catalase (e.g. Composition B) was not sufficiently stable at 141 days.

As also demonstrated in the forthcoming examples, aqueous compositions of 1,3 propane diol and catalase (e.g. composition B) were found to be sufficiently stable, as described above, for 32, 67, and 100 days, or any suitable range between and including any two of these values. The concentration of dipropylene glycol is typically at least 5, 5.5, 6, 6.5, 7, 7.5, 8.5, 9, 9.5, or 10 wt. % of the aqueous solution of 1,3 propane diol and catalase (e.g. composition B). In some embodiments, the concentration of dipropylene glycol is at least 11, 12, 13, 14, or 15 wt. % of the aqueous solution of 1,3 propane diol and catalase (e.g. composition B). When the amount of dipropylene glycol was greater than 17 wt. %, the aqueous composition comprising catalase (e.g. composition B) was not sufficiently stable at 141 days.

In some embodiments, composition B further comprises a buffer having a pH of 7-8. Although the enzyme activity may be about the same for a pH ranging from 3 to 9; a more neutral pH can be preferred for an oral cavity.

Generally, composition A is applied to the tooth surface before or after the composition B is applied to the tooth surface. In some embodiments, composition A is applied at least 30 seconds before or after composition B is applied. Either composition A or composition B can be (independently) in any form suitable for oral cavity delivery, such as in the form of aqueous solutions (e.g., a rinse), an aqueous gel, an aqueous paste. In some embodiments, composition A and composition B can be (independently) applied as rinses. In another embodiment, composition A can be applied as a gel and composition B can be applied as a rinse.

In some embodiments, the oral cavity and teeth are exposed to composition A for a relatively short exposure time, such that no noticeable bleaching is observed by the naked eye when the method is performed. (e.g. in a single application of composition A, or multiple applications). In some embodiments, composition A or composition B are independently applied for an exposure time of less than 1 hour, less than 30 minutes, less than 10 minutes, less than 5 minutes, less than 2 minutes, or less than 1 minute. In some of these embodiments, composition A or composition B is independently applied for 10 minutes, 5 minutes, 2 minutes, 1 minute, 30 seconds, 15 seconds or a range between and including any two of these values.

As the hydrogen peroxide adduct or hydrogen peroxide precursor is applied to the tooth, it dissociates in the environment within the oral cavity to produce hydrogen peroxide. Hydrogen peroxide in the presence of peroxidase, e.g., catalase can cause release of oxygen, thereby loosening the calculus from the tooth.

After composition A and composition B are applied, at least a part of the calculus can be removed from the tooth by any suitable mechanical means, e.g., scaling (such as using a dental scaler), brushing, swabbing, wiping, ultrasonic, air polishing or jetted water. In some embodiments, the part of the calculus may be removed by mechanical means other than toothbrushing, for example by a dental scaler. In some embodiments, the removing step occurs within 1 day, 12 hours, 6 hours, 3 hours, 1 hour, 30 minutes, and preferably withing 10 minutes, 5 minutes, 2 minutes, 1 minute, 30 seconds, or 15 seconds after the step of applying composition A and B.

In some embodiments, additives can be applied to the tooth surface. In some embodiments, composition A and/or composition B additives comprise additives. Additives can include, but are not limited to, antiseptics and preservatives, antibiotics, flavoring materials, surfactants, abrasives, thickeners and binders, propellants, carriers, tartar control agents, calcium sequestrants, fluoride salts, and dyes.

In some embodiments, the aqueous compositions further comprise thickeners, such as hydroxy ethyl cellulose, in an amount not greater than 2, 1.5, 1, or 0.5 wt. % of the aqueous compositions (e.g. composition A and/or composition B). The aqueous compositions (e.g. composition A and/or composition B) typically do not contain additives that would react with the hydroxyl groups of the stabilizer. Thus, the composition is typically free of amine compounds such as polyethoxylated alkyl diamine and amine oxide.

Suitable antiseptics and preservatives include, but are not limited to, chlorhexidine and salts thereof, polyhexamethylene biguanide, octenidine, quaternary ammonium salts and polymers thereof, organic acids, chelating agents for example a calcium chelating agent (e.g., Ethylenediaminetetraacetic acid (EDTA)), essential oils, and parabens. Examples of antiseptics and preservatives can include those described in U.S. Pat. No. 8,647,608. Non-limiting examples of antibiotics can include penicillin, tetracycline, minocycline, and the like. Examples of antibiotics can also include those described in U.S. Pat. No. 6,685,921. Examples of flavoring materials can include artificial sweeteners, plant oils, and synthetic flavors. Examples of abrasives can include silica particles, synthetic inorganic particles, and synthetic or plant derived organic particles. Suitable surfactants can include those described in U.S. Publication No. 2006/0051385. Examples of such surfactants include cationic surfactants, zwitterionic surfactants, non-ionic surfactants and anionic surfactants. Examples of thickeners can include glycerol, silica, cellulose-based polymers, plant gums (e.g. guar and xanthan gum), petroleum derived materials such as petrolatum, polyethylene glycols, polyvinyl pyrrolidone and co-polymers thereof, polylactic acids, long chain fatty acid alcohols, and acrylate polymers. Suitable binders can include those described in U.S. Pat. No. 8,647,608. Suitable carriers can include those described in U.S. Pat. No. 8,647,608. Carriers can include any alcohols suitable for use in a subject's oral cavity, including ethanol and isopropanol and glycerol. Suitable dyes include those described in U.S. Pat. No. 8,647,608. Examples of tartar control agents include those described in U.S. Pat. No. 6,685,921. Anti-tartar agents known for use in dental care products can include, but are not limited to, phosphate. Phosphates can include pyrophosphates, polyphosphates, polyphosphonates and mixtures thereof. Pyrophosphate salts can include the dialkali metal pyrophosphate salts, tetraalkali metal pyrophosphate salts and mixtures thereof. Examples of fluoride salts can include those described in U.S. Pat. Nos. 6,685,921, 3,535,421 and 3,678,154.

Materials

TABLE 1

| Material | Source |
|---|---|
| Catalase 20,000 Powder<br>Catalase<br>Enzyme | Specialty Enzymes and<br>Biotechnology, Chino, CA |
| Phosphate buffered saline,<br>pH 7.4 (1X) | Thermo Fisher Scientific,<br>Waltham, MA |
| Glycerol Comparative<br>Molecular weight = 94 g/mole<br>Molecular weight/oxygen atom<br>(e.g. hydroxyl group) = 31 | Cargill, Wayzata, MN |
| Thymol (antimicrobial<br>preservative) | Spectrum Chemical, New<br>Brunswick, NJ |
| Dipropylene glycol - mixture<br>of isomers<br>Molecular weight = 134 g/mole<br>Molecular weight/<br>oxygen atom = 45 | Alfa Aesar, Haverhill, MA |
| Propylene glycol<br>Molecular weight = 76 g/mole<br>Molecular weight/oxygen = 38 | Sigma Aldrich, St. Louis, MO |
| 1,3-Propanediol<br>Molecular weight = 76 g/mole<br>Molecular weight/oxygen<br>atom = 38 | Alfa Aesar, Haverhill, MA |
| NATROSOL 250 Hydroxyethyl<br>cellulose (HEC) | Ashland Chemicals,<br>Wilmington, DE |
| Hydrogen peroxide, USP, 3% | Hydrox Laboratories, Elgin, IL |
| Sodium azide | Sigma Aldrich, St. Louis, MO |

Catalase Enzyme Stability Assay

Catalase enzyme decomposes hydrogen peroxide to oxygen and water. The measurement of residual hydrogen peroxide in the reaction of a catalase enzyme formulation with hydrogen peroxide was used to indicate catalase activity. Catalase enzyme formulations which remained stable on storage continued to decompose hydrogen peroxide, resulting in low concentrations of remaining hydrogen peroxide after reaction of the stored catalase enzyme formulation with fresh hydrogen peroxide. However, catalase enzyme formulations in which the enzyme was degraded on storage were less effective at decomposing hydrogen peroxide, resulting in high concentrations of remaining hydrogen peroxide after reaction of the stored catalase enzyme formulation with fresh hydrogen peroxide.

Formulation samples were submitted to accelerated ageing conditions by storing sealed glass containers of catalase enzyme formulations in a stability chamber set at a constant temperature of 37° C. Samples were tested at various storage time points according to the following procedure. An aliquot (200 microliters) of the stored catalase formulation was combined with 200 microliters of a 3% hydrogen peroxide solution in a glass vial and the contents were mixed for 2 seconds using a vortex mixer at maximum speed followed by allowing the reaction to proceed for 60 seconds. The reaction was then neutralized by adding with mixing 400 microliters of an aqueous 20 mM sodium azide solution. The concentration of catalase was 1,000 U/g.

The residual concentration of hydrogen peroxide in the reaction solution was measured using a semi-quantitative, colorimetric, measurement strip (QUANTOFIX Peroxide 1000 Strips, obtained from Macherey-Nagel Incorporated, Düren, Germany) according to the manufacturer's instructions. The test strips were evaluated by visual examination using a color-scale comparison chart provided by the manufacturer. The comparison chart had six different colors that corresponded to 0-50 mg/L, 150 mg/L, 300 mg/L, 500 mg/L, 800 mg/L and 1000 mg/L of hydrogen peroxide. Prior to submitting to the stability chamber, each formulation was tested for baseline catalase activity within 24 hours of preparation. All of the formulations submitted for stability testing had a baseline test result of 0-50 mg/L residual hydrogen peroxide indicating significant catalase activity.

For aged formulation samples, measurement of 0-50 mg/L of residual hydrogen peroxide after reaction with the catalase formulation indicated that the formulation maintained significant catalase activity that was equivalent to the baseline catalase activity, while the measurement of >50 mg/L of hydrogen peroxide in the sample indicated that the activity of the catalase enzyme in the formulation was significantly diminished compared to baseline. The last time point (in days of storage) at which the catalase activity was determined to be equivalent to the baseline catalase activity (i.e., 0-50 mg/L of hydrogen peroxide measured) was reported as the "Days of Maximum Catalase Activity".

Example 1. Catalase Enzyme Formulations Containing Dipropylene Glycol

Formulations A1-A6 were individually prepared by the following procedure. A solution of dipropylene glycol containing thymol was maintained at 37° C. for 1-2 hours and then cooled to room temperature. Thymol was included in the formulation as preservative to inhibit microbial growth. This solution was then added with mixing to a glass jar containing a solution of catalase enzyme in PBS. Additional formulations (B1-B6), were prepared in which HEC was added with stirring to each formulation. The jars containing the finished formulations were sealed and stored at 37° C. in a stability chamber. All of the final formulations contained 5 wt. % of catalase enzyme, varying concentrations of dipropylene glycol, and 0.1 wt. % of thymol. Formulations D1-D6 contained 0.5 wt. % of HEC. The total weight of each finished formulation was 10 g. The concentrations of the compositions in the formulations are reported in Table 2.

The stability of the catalase enzyme in the formulations was determined according to the "Catalase Enzyme Stability Assay" described above. Catalase activity was tested at storage time points of 6, 28, 42, 97, 141, 161, 193, 222, and 260 days. The formulation jars were returned to the stability chamber immediately after testing. In Table 2, the last time point (in days of storage) at which the catalase activity was determined to be equivalent to the baseline catalase activity (i.e., 0-50 mg/L of hydrogen peroxide measured) is reported.

TABLE 2

| Formulation | Catalase (wt. %) | Dipropylene glycol (wt. %) | HEC (wt.%) | Days of Maximum Catalase Activity (Formulation stored at 37° C.) |
|---|---|---|---|---|
| Control | 5 | 0 | 0 | 6 |
| A-1 | 5 | 2.4 | 0 | 42 |
| A-2 | 5 | 3.2 | 0 | 42 |
| A-3 | 5 | 4.7 | 0 | 42 |
| A-4 | 5 | 6.3 | 0 | 97 |
| A-5 | 5 | 7.1 | 0 | 141 |
| A-6 | 5 | 9.5 | 0 | 193 |
| Control | 5 | 0 | 0.5 | 6 |
| B-1 | 5 | 2.4 | 0.5 | 42 |
| B-2 | 5 | 3.2 | 0.5 | 42 |
| B-3 | 5 | 4.7 | 0.5 | 42 |
| B-4 | 5 | 6.3 | 0.5 | 97 |
| B-5 | 5 | 7.1 | 0.5 | 141 |
| B-6 | 5 | 9.5 | 0.5 | 222 |

Example 2. Catalase Enzyme Formulations Containing Dipropylene Glycol

Formulations C1-C6 and D1-D6 were individually prepared following the procedure described in Example 1. The final formulations contained 5 wt. % of catalase enzyme, varying concentrations of dipropylene glycol, and 0.05 wt. % of thymol. Formulations D1-D6 contained 0.5 wt. % of HEC. The total weight of each finished formulation was 20 g. The concentrations of the compositions in the formulations are reported in Table 3.

The stability of the catalase enzyme in the formulations was determined according to the "Catalase Enzyme Stability Assay". Catalase activity was tested at storage time points of 32, 67, 100, and 141 days. The formulation jars were returned to the stability chamber immediately after testing. In Table 3, the last time point (in days of storage) at which the catalase activity was determined to be equivalent to the baseline catalase activity (i.e., 0-50 mg/L of hydrogen peroxide measured) is reported.

TABLE 3

| Formulation | Catalase (wt. %) | Dipropylene glycol (wt. %) | HEC (wt. %) | Days of Maximum Catalase Activity (Formulation stored at 37° C.) |
|---|---|---|---|---|
| C-1 | 5 | 5.0 | 0 | 67 |
| C-2 | 5 | 10.5 | 0 | 141* |
| C-3 | 5 | 14 | 0 | 141* |
| C-4 | 5 | 16.6 | 0 | 141* |
| C-5 | 5 | 20.6 | 0 | 141* |
| C-6 | 5 | 23.4 | 0 | 141* |
| D-1 | 5 | 5.0 | 0.5 | 67 |
| D-2 | 5 | 10.5 | 0.5 | 141* |
| D-3 | 5 | 14 | 0.5 | 141* |
| D-4 | 5 | 16.6 | 0.5 | 141* |
| D-5 | 5 | 20.6 | 0.5 | 141* |
| D-6 | 5 | 23.4 | 0.5 | 141* |

*indicates that catalase activity was maintained at the baseline level (i.e., 0-50 mg/L of hydrogen peroxide was measured) on the last date tested (day 141)

Example 3. Catalase Enzyme Formulations Containing Dipropylene Glycol

Formulations E1-E3 and F1-F3 were individually prepared following the procedure described in Example 1. The final formulations contained 5 wt. % of catalase enzyme, varying concentrations of dipropylene glycol, and 0.05 wt. % of thymol. Formulations F1-F3 contained 0.5 wt. % of HEC. The total weight of each finished formulation was 5 g. The concentrations of the compositions in the formulations are reported in Table 4.

The stability of the catalase enzyme in the formulations was determined according to the "Catalase Enzyme Stability Assay". Catalase activity was tested at storage time points of 13, 90, 146, and 160 days. The formulation jars were returned to the stability chamber immediately after testing. In Table 4, the last time point (in days of storage) at which the catalase activity was determined to be equivalent to the baseline catalase activity (i.e., 0-50 mg/L of hydrogen peroxide measured) is reported.

TABLE 4

| Formulation | Catalase (wt. %) | Dipropylene glycol (wt. %) | HEC (wt. %) | Days of Maximum Catalase Activity (Formulation stored at 37° C.) |
|---|---|---|---|---|
| E-1 | 5 | 9.4 | 0 | 146 |
| E-2 | 5 | 19.0 | 0 | 90 |
| E-3 | 5 | 28.4 | 0 | <13 |
| F-1 | 5 | 9.4 | 0.5 | 146 |
| F-2 | 5 | 19.0 | 0.5 | 90 |
| F-3 | 5 | 28.4 | 0.5 | <13 |

**indicates that catalase activity was less than the baseline level (i.e., >50 mg/L of hydrogen peroxide was measured) on the first date tested (day 13)

Example 4. Catalase Enzyme Formulations Containing 1-3 Propanediol

Formulations G1-G8 and H1-H8 were individually prepared following the procedure described in Example 1 with the exception that dipropylene glycol was replaced in the formulations with 1-3 propanediol. The final formulations contained 5 wt. % of catalase enzyme, varying concentrations of 1,3-propanediol, and 0.05 wt. % of thymol. The total weight of each finished formulation was 20 g. The concentrations of the compositions in the formulations are reported in Table 5.

The stability of the catalase enzyme in the formulations was determined according to the "Catalase Enzyme Stability Assay". Catalase activity was tested at storage time points of 32, 67, 100, and 141 days. The formulation jars were returned to the stability chamber immediately after testing. In Table 5, the last time point (in days of storage) at which the catalase activity was determined to be equivalent to the baseline catalase activity (i.e., 0-50 mg/L of hydrogen peroxide measured) is reported.

TABLE 5

| Formulation | Catalase (wt. %) | 1,3-Propanediol (wt. %) | HEC (wt. %) | Days of Maximum Catalase Activity (Formulation stored at 37° C.) |
|---|---|---|---|---|
| G-1 | 5 | 2.8 | 0 | 32 |
| G-2 | 5 | 4.8 | 0 | 32 |
| G-3 | 5 | 6.7 | 0 | 32 |
| G-4 | 5 | 9.5 | 0 | 67 |
| G-5 | 5 | 11.4 | 0 | 67 |
| G-6 | 5 | 14.3 | 0 | 100 |
| G-7 | 5 | 17.1 | 0 | 141* |
| G-8 | 5 | 19.0 | 0 | 141* |
| H-1 | 5 | 2.8 | 0.5 | 32 |
| H-2 | 5 | 4.8 | 0.5 | 32 |
| H-3 | 5 | 6.7 | 0.5 | 67 |
| H-4 | 5 | 9.5 | 0.5 | 67 |
| H-5 | 5 | 11.4 | 0.5 | 67 |
| H-6 | 5 | 14.3 | 0.5 | 141* |
| H-7 | 5 | 17.1 | 0.5 | 141* |
| H-8 | 5 | 19.0 | 0.5 | 141* |

*indicates that catalase activity was less than the baseline level (i.e., 0-50 mg/L of hydrogen peroxide was measured) on the last date tested (day 141)

Example 5. Catalase Enzyme Formulations Containing Propylene Glycol

Formulations of Examples I-11 to I-26 (20 g total weight) were individually prepared by following procedure described in Example 1 with the exception that dipropylene glycol was replaced in the formulations with propylene glycol. The concentrations of the compositions in the formulations are reported in Table 6.

The stability of the catalase enzyme in the formulations was determined according to the "Catalase Enzyme Stability Assay. Catalase activity was tested at storage time points of 32 and 66 days. The formulation jars were returned to the stability chamber immediately after testing. In Table 6, the last time point (in days of storage) at which the catalase activity was determined to be equivalent to the baseline catalase activity (i.e., 0-50 mg/L of hydrogen peroxide measured) is reported.

TABLE 6

| Formulation | Catalase (wt. %) | Propylene Glycol (wt. %) | HEC (wt. %) | Days of Maximum Catalase Activity (Formulation stored at 37° C.) |
|---|---|---|---|---|
| I-11 | 5 | 2.8 | 0 | <32** |
| I-12 | 5 | 4.7 | 0 | <32** |
| I-13 | 5 | 6.6 | 0 | 32 |
| I-14 | 5 | 9.5 | 0 | 32 |
| I-15 | 5 | 11.4 | 0 | 32 |
| I-16 | 5 | 14.2 | 0 | 32 |
| I-17 | 5 | 17.1 | 0 | 32 |
| I-18 | 5 | 19.0 | 0 | 32 |
| I-19 | 5 | 2.8 | 0.5 | 32 |
| I-20 | 5 | 4.7 | 0.5 | 32 |
| I-21 | 5 | 6.6 | 0.5 | <32** |
| I-22 | 5 | 9.5 | 0.5 | 32 |
| I-23 | 5 | 11.4 | 0.5 | <32** |
| I-24 | 5 | 14.2 | 0.5 | 32 |
| I-25 | 5 | 17.1 | 0.5 | 32 |
| I-26 | 5 | 19.0 | 0.5 | 32 |

**indicates that catalase activity was less than the baseline level (i.e., >50 mg/L of hydrogen peroxide was measured) on the first date tested (day 32)

Comparative Example A. Catalase Enzyme Formulations Containing Glycerol

Formulations of Comparative Examples CE-A1 to CE-A10 (5 g total weight) were individually prepared by following the procedure described in Example 1 with the exception that dipropylene glycol was replaced in the formulations with glycerol. The concentrations of the compositions in the formulations are reported in Table 6.

The stability of the catalase enzyme in the formulations was determined according to the "Catalase Enzyme Stability Assay". Catalase activity was tested at a storage time point of 68 days. The formulation jars were returned to the stability chamber immediately after testing. In Table 7, the last time point (in days of storage) at which the catalase activity was determined to be equivalent to the baseline catalase activity (i.e., 0-50 mg/L of hydrogen peroxide measured) is reported.

TABLE 7

| Formulation | Catalase (wt. %) | Glycerol (wt. %) | HEC (wt. %) | Days of Maximum Catalase Activity (Formulation stored at 37° C.) |
|---|---|---|---|---|
| CE-A1 | 5 | 9.4 | 0 | <68** |
| CE-A2 | 5 | 19.0 | 0 | <68** |
| CE-A3 | 5 | 28.4 | 0 | <68** |
| CE-A4 | 5 | 51.0 | 0 | <68** |
| CE-A5 | 5 | 66.4 | 0 | <68** |
| CE-A6 | 5 | 9.4 | 0.5 | <68** |
| CE-A7 | 5 | 19.0 | 0.5 | <68** |
| CE-A8 | 5 | 28.4 | 0.5 | <68** |
| CE-A9 | 5 | 51.0 | 0.5 | <68** |
| CE-A10 | 5 | 66.4 | 0.5 | <68** |

**indicates that catalase activity was less than the baseline level (i.e., >50 mg/L of hydrogen peroxide was measured) on the first date tested (day 68)

What is claimed is:

1. A method of removing calculus from a tooth comprising:

applying aqueous compositions A and B to a tooth surface, wherein composition A comprises hydrogen peroxide or a precursor thereto and composition B comprises catalase and a stabilizer selected from dipropylene glycol and 1,3-propane-diol, wherein composition B is sufficiently stable such that after storage for at least 75 days at 37° C. composition B comprises less than 50 mg/L of hydrogen peroxide when reacted with a 3% hydrogen peroxide aqueous solution; and removing at least a part of the calculus from the tooth surface.

2. The method of claim 1 wherein composition B is sufficiently stable such that after storage for at least 100 days at 37° C. composition B comprises less than 50 mg/L of hydrogen peroxide when reacted with a 3% hydrogen peroxide aqueous solution.

3. The method of claim 1 wherein the stabilizer comprises an alkylene or ether backbone and at least two hydroxyl groups.

4. The method of claim 3 wherein the stabilizer has a molecular weight per oxygen atom of at least 32, 33, 34, 35, 36, 37, or 38 g/mole.

5. The method of claim 1 wherein the stabilizer is miscible with deionized water.

6. The method of claim 1 wherein the stabilizer is dipropylene glycol.

7. The method of claim 1 wherein the stabilizer is present in an amount ranging from 5 wt. % to 15 wt. % of the total aqueous composition.

8. The method of claim 1 wherein composition B further comprises a buffer having a pH of 7-8.

9. The method of claim 1 wherein the catalase is isolated from plants or fungi.

10. The method of claim 1 wherein composition B further comprises additives including an antimicrobial.

11. The method of claim 1 wherein composition A comprises 1 wt. % to 10 wt. % hydrogen peroxide or a precursor thereto providing 1 wt. % to 10 wt. % hydrogen peroxide.

12. The method of claim 1 wherein composition A is applied before composition B.

13. The method of claim 1 wherein composition B is applied before composition A.

14. An aqueous composition for removing calculus from a tooth surface, the aqueous composition comprising:

catalase; and a stabilizer selected from dipropylene glycol and 1,3-propane-diol;

wherein after storage for at least 75 days at 37° C. the aqueous composition comprises less than 50 mg/L of hydrogen peroxide when reacted with a 3% hydrogen peroxide aqueous solution.

15. The aqueous composition of claim 14 wherein the stabilizer is dipropylene glycol.

16. The aqueous composition of claim 14 wherein after storage for at least 100 days at 37° C. the aqueous composition comprises less than 50 mg/L of hydrogen peroxide when reacted with a 3% hydrogen peroxide aqueous solution.

17. The aqueous composition of claim 14 wherein the stabilizer is present in an amount ranging from 5 wt. % to 15 wt. % of the total aqueous composition.

18. The aqueous composition of claim 14 wherein the composition is free of amine compounds.

19. A kit comprising:

a composition A comprising hydrogen peroxide or a precursor thereto; and a composition B comprising catalase and a stabilizer selected from dipropylene glycol and 1,3-propane-diol, wherein composition B is sufficiently stable such that after storage for at least 75 days at 37° C. composition B comprises less than 50 mg/L of hydrogen peroxide when reacted with a 3% hydrogen peroxide aqueous solution.

20. The kit of claim 19 wherein composition B is sufficiently stable such that after storage for at least 100 days at 37° C. composition B comprises less than 50 mg/L of hydrogen peroxide when reacted with a 3% hydrogen peroxide aqueous solution.

* * * * *